United States Patent [19]

Grenier et al.

[11] E Re. 30,140

[45] Reissued Nov. 6, 1979

[54] METHOD FOR COOLING A GASEOUS MIXTURE TO A LOW TEMPERATURE

[75] Inventors: Maurice Grenier, Paris; Pierre Petit, Chatenay Malabry, both of France

[73] Assignee: Compagnie Francaise d'Etudes et de Construction Technip, Paris, France

[21] Appl. No.: 501,246

[22] Filed: Aug. 28, 1974

Related U.S. Patent Documents

Reissue of:

[64] Patent No.: 3,274,787
Issued: Sep. 27, 1966
Appl. No.: 484,541
Filed: Sep. 2, 1965

U.S. Applications:

[63] Continuation of Ser. No. 273,338, Jul. 19, 1972.

[51] Int. Cl.[2] ..... F25J 3/02
[52] U.S. Cl. ..... 62/28; 62/40
[58] Field of Search ..... 62/9, 11, 40, 28

[56] References Cited

U.S. PATENT DOCUMENTS

| | | | |
|---|---|---|---|
| 2,041,725 | 5/1936 | Podbielniak | 62/40 |
| 2,936,593 | 5/1960 | Greenberg | 62/23 |
| 2,973,834 | 3/1961 | Cicalese | 62/23 |
| 3,205,669 | 9/1965 | Grossmann | 62/23 |
| 3,593,535 | 7/1971 | Gaumer et al. | 62/23 |

FOREIGN PATENT DOCUMENTS

| | | | |
|---|---|---|---|
| 665385 | 6/1963 | Canada | 62/40 |
| 895094 | 5/1962 | United Kingdom | 62/40 |

OTHER PUBLICATIONS

Kleemenko, "One Flow Cascadie Cycle," pp. 34–39, of "Progress in Refrigeration Science and Technology."

*Primary Examiner*—Norman Yudkoff
*Attorney, Agent, or Firm*—Frishauf, Holtz, Goodman & Woodward

EXEMPLARY CLAIM

*8. A method for cooling a second gaseous mixture to low temperature and producing at least one constituent of said mixture in liquid phase, comprising:*

*a. cooling and subjecting first gaseous mixture containing at least one component of said secong gaseous mixture, to a fractionate condensation under a first pressure,*

*b. expanding at least two condensed fractions obtained during the fractionate condensation of said first gaseous mixture, reuniting the expanded condensed fractions with said first gaseous mixture under a second pressure lower than said first pressure, vaporizing and reheating the reunited fractions with said first gaseous mixture under said second pressure, by heat exchange with said second gaseous mixture undergoing cooling, and with said first gaseous mixture undergoing fractionate condensation, and recompressing said first gaseous mixture to said first pressure,*

*c. reuniting under said first pressure said second gaseous mixture undergoing cooling with said first gaseous mixture undergoing fractionate condensation, when said gaseous mixture is in conditions of temperature and pressure such that a major portion of said constituent to be produced in liquid phase is condensed within said second gaseous mixture, and after the first condensed fraction of said first gaseous mixture has been withdrawn for expansion and vaporization, continuing the fractionate condensation of the mixture so obtained under said first pressure until there is obtained a last condensed fraction containing a major part of said constituent to be produced in liquid phase,*

*d. expanding to said second pressure the last condensed fraction, and separating the last expanded fraction into a liquid portion expanded to a pressure lower than said second pressure and a residual gaseous portion for recompression with said first gaseous mixture, and withdrawing said last expanded liquid portion as a product stream, and*

*e. prior to reuniting said first gaseous mixture and said second gaseous mixture, condensing at least partially said second gaseous mixture under a third pressure which is higher than said first pressure, and expanding said second gaseous mixture at least partially condensed to said first pressure.*

2 Claims, 2 Drawing Figures

METHOD FOR COOLING A GASEOUS MIXTURE TO A LOW TEMPERATURE

Matter enclosed in heavy brackets [ ] appears in the original patent but forms no part of this reissue specification; matter printed in italics indicates the additions made by reissue.

This is a continuation of application Ser. No. 273,338, filed July 19, 1972.

The invention relates to a method for cooling a gaseous mixture to low temperatures and producing at least one constituent of this mixture in the liquid state, wherein the gaseous mixture is subjected to a fractionate condensation, and the constituent to be produced in the liquid state, after its condensation, is expanded to the pressure at which it is to be produced, then is wholly withdrawn, while at least one of the condensed fractions is expanded and vaporized in heat exchange with the gaseous mixture undergoing fractionate condensation, under a higher pressure than the pressure of withdrawal of the constituent to be produced in the liquid state, then recompressed and reunited to the gaseous mixture to be cooled, characterised in that said gaseous mixture is used as a frigorific fluid within a cooling cycle providing the condensation of a second gaseous mixture consisting of the same main components, and during its cooling is not added to said second gaseous mixture until at a temperature level low enough so that the constituent to be produced in the liquid state be at least mostly condensed within said second gaseous mixture.

It further comprises the following features, either individually or in any combination:

(1) If the gaseous mixture is available at a comparatively high pressure, the vaporized fraction is recompressed only to a lower pressure than that of the gaseous mixture, then cooled independently thereof, and is added to the latter only at a temperature level at which the constituent of the gaseous mixture of gases to be separated in the liquid state is already liquefied at least for its major portion;

(2) The gaseous mixture is used as refrigerating fluid passing through a closed cycle to ensure the fractionated condensation of another gaseous mixture comprising the same main constituents, wherein all the expanded and vaporized fractions coming from the first mixture of gases are reunited so as to reconstitute the first mixture of gases after their reheating and recompression;

(3) At least a part of a fraction separated during the fractionated condensation of the other gaseous mixture is reunited with the fraction expanded during the vaporizing of the first gaseous mixture so as to compensate for losses in the circuit of the latter and/or to adjust its composition;

(4) At least one part of a fraction separated during the fractionated condensation of the first mixture of gases, acting as refrigerating fluid, is combined with a fraction separated from the other mixture of gases so as to adjust the composition of the first mixture.

The improvement of the invention, and especially that according to (1), makes it possible to use better the cold output resulting from the free expansion of the gaseous mixture of which one constituent is to be produced in the liquid state, without, however, effecting the recycling of the fraction or fractions revaporized and recompressed under a pressure which is economically too high.

The improvement according to (2) facilitates the control of an installation for carrying out the method and provides smaller heat exchange surfaces. Combined with the variations according to (3) and possibly (4), it makes it possible to adapt the composition of the recycled gas to that of the gaseous mixture, of which one constituent is to be produced in the liquid state, in the case in which a gaseous mixture of variable composition is being treated.

The invention will be further described, by way of non-limitative example with reference to the accompanying drawings, showing two installations for liquefying natural gas and comprising the improvements defined above.

Figure 1:
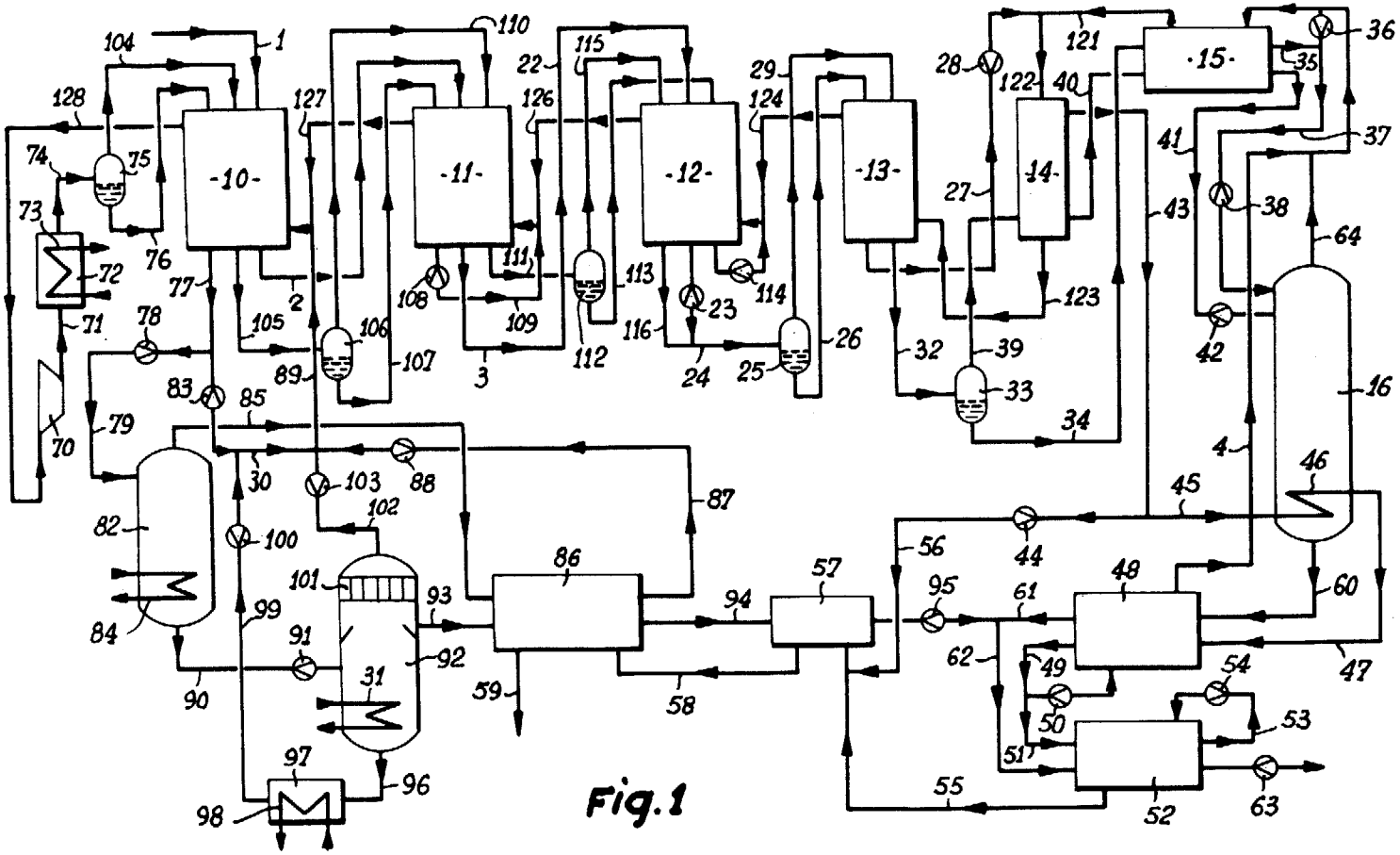
FIG. 1 shows an installation for liquefying natural gas in which the latter, available at a comparatively high pressure, is expanded to a pressure equal to that of the recycled gas and is added thereto only after the major part of the methane it contains has been liquefied.

The installation of FIG. 1 comprises substantially cooling and liquefying exchangers, 10, 11, 12, 13, 14 and 15, common to the circuits for the natural gas to be liquefied and for the recycling gas, a fractionating column 16, or degassing column, in which nitrogen is removed from the liquefied mixture, and fractionating columns 82 and 92 in which the heavy hydrocarbons (butane, propane) are separated.

The natural gas to be liquefied, available at 30° C. and at an absolute pressure of 50 bars absolute and having for example, the following composition:

| | Percent by volume |
|---|---|
| Methane | 85 |
| Ethane | 7 |
| Propane | 3 |
| Butanes | 3 |
| Nitrogen and other light gases | 2 |

is introduced through a conduit 1 into the exchanger 10 where it is cooled to about −12° C., concurrently with the gas recycled at high pressure and a liquid fraction rich in butanes separated from the latter, and in indirect heat exchange with the gas recycled at low pressure. The cooled mixture is already partly liquefied and passes through the conduit 2 to an exchanger 11 where it is cooled to −48° C. in heat exchange with the recycled gas; its condensation continues.

The liquid-gas mixture which results is then passed through a conduit 3 to an exchanger 12 where it is cooled down to −72° C.; it is then completely liquefied. It is then expanded in a valve 23 to about 7 bars absolute pressure, mixed with the recycled gas supplied through a conduit 116 and introduced through a conduit 24 into a separator 25. The liquid collected at the bottom of the separator passes through a conduit 26 into an exchanger 13 where it is undercooled to about −85° C. and then recombined through the conduit 27 and an expanding valve 28 with the volatile recycled gas at the cold end of the exchanger 14. The gas coming from the separator 25 passes through a conduit 29 to the exchanger 13 where it is cooled to −97° C.; a substantial part liquefies. The mixture of liquid and vapor passes through the conduit 32 into the separator 33. The liquid accumulating at the bottom of the separator and comparatively rich in ethane passes through a conduit 34 to an exchanger 15 where it is undercooled to about −127° C. It is removed through a conduit 35. A fraction may be recombined through an expanding valve 36 with the volatile gas rich in nitrogen issuing from the degasing tower 16. The other fraction passes through a conduit 37 and an expanding valve 38 to 7 bars to the top of the degassing tower 16 where nitrogen and other highly volatile gases are removed.

The gaseous fraction removed from the separator 33 through the conduit 39 is again partly refrigerated and condensed in the reflux type exchanger 14. The formed liquid consisting substantially of methane and containing little ethane is passed through the conduit 40 to the exchanger 15 where it is undercooled to about −127° C., then through a conduit 41 and the 7 bars expanding valve 42 into the upper part of the tower 16. The residual nonliquefied gas in the exchanger 14 is evacuated through a conduit 43. A part is expanded near atmospheric pressure in the valve 44 and recombined through a conduit 56 with the residual mixture of methane and nitrogen, to be evacuated prior to its reheating. The other part flows through the conduit 45 into the coil 46 located in the sump of the degasing tower 16 where it is liquefied whilst heating the bottom of this column. It passes then through a conduit 47 into an exchanger 48, where it is undercooled concurrently with the natural liquefied gas. This portion is evacuated through a conduit 49 and is then divided into two fractions. The first fraction, expanded in a valve 50 at about 7 bars, is passed in counter-current through the exchanger 48 where it effects the undercooling of the liquid and then recombines through the conduit 4 with the vapours discharged at the head of the degasing tower 16. The second fraction passes through a conduit 51 into an exchanger 52 where it is again undercooked, then in counter-current through the same heat exchanger through a conduit 53 and an expanding valve 54 to near atmospheric pressure. This produces the final undercooling of the natural gas product. It is then evacuated through a conduit 55 to an exchanger 57 through which it passes after addition of the first part of the residual gas already mentioned through the conduit 56. After reheating in this exchanger and then in the exchanger 86, to which it is supplied through a conduit 58, in heat exchange with the heavier hydrocarbons (propane, butanes) which are to be added to the liquefied natural gas, it is removed through a conduit 59 and is used, for example, as fuel for boilers, owing to its high methane content.

The liquid introduced into the degasing tower 16 is here separated into a liquid product free from nitrogen, withdrawn from the vessel through a conduit 60, and into vapours rich in nitrogen, removed from the top through a conduit 64. The liquid product is undercooled in the exchanger 48. After the addition of heavier liquid hydrocarbons separated in the fractionating column 92 through the expanding valve 95, it is subjected to a further undercooling in the exchanger 52. The liquefied and undercooled gas is finally expanded in the valve 63 to near atmospheric pressure for its introduction into the storage tank (not shown).

The vapours rich in nitrogen, taken from the top of the tower 16 through the conduit 64, are added through the conduit 4 to the fraction vaporized in the exchanger 48 and then through the expanding valve 36 to a fraction of the liquid coming from the separator 33 and undercooled in the exchanger 15. The whole is then vaporized and reheated in the exchanger 15, leaves the same through a conduit 121, is added through the expanding valve 28 to the liquid recovered in the separator 25 and undercooled in the exchanger 13. The whole is vaporized and reheated in the exchanger 14 and passes through the conduit 123 to the exchanger 13 where it is further reheated. It flows then through the conduit 124 into the exchanger 12, after addition through the expanding valve 114 of the liquid recovered in the separator 112 and undercooled in the exchanger 12. The mixture of gas and liquid is vaporized and reheated in the exchanger 12, flows then through the conduit 126 to the exchanger 11, after addition through the expanding valve 108 and conduit 109 of the liquid recovered in the separator 106 and undercooled in the exchanger 11. The mixture of gas and liquid is vaporized and reheated in the exchanger 11, passes then through the conduit 127 into the exchanger 10 after addition through the conduit 89 of part of the liquid recovered in the separator 75 and of liquid and gaseous fractions coming from the fractionating columns 82 and 92, the operation of which is described further below. The mixture of gas and liquid is vaporized and heated near ambient temperature in the exchanger 10 and is then evacuated through the conduit 128.

The gaseous mixture formed in this way and reheated is then compressed by a turbo-compressor 70 to a pressure of about 30 bars. The compressed mixture passes through a conduit 71 to a cooler 72 equipped with a water cooling coil 73. A fraction consisting mainly of heavy hydrocarbons is condensed and arrives with the remaining gas through the conduit 74 in the separator 75.

The liquid rich in butanes, recovered at the bottom of the separator, passes through the conduit 76 into the exchanger 10 where it is undercooled and from which it is removed through the conduit 77. It is then divided into two parts. A first part is expanded in the valve 83 and combined with different other expanded liquid and gaseous fractions, whose origin will be discussed below, and is introduced therewith into the recycled gaseous low-pressure mixture at the cold end of the exchanger 10. The second part is expanded in the valve 78 to about 15 bars and then introduced through the conduit 79 into the fractionating column 82.

In the column 82, heated at the bottom by a steam coil 84, the liquid fraction is separated into comparatively volatile vapours and a residual liquid. The vapours pass through the conduit 85 to the exchanger 86 where they are cooled in heat exchange with the residual mixture of nitrogen and methane, and are then returned through the conduit 87, the expanding valve 88 and the conduit 89 to the low pressure gas mixture at the cold end of the exchanger 10.

The liquid removed from the bottom of the column 82 through the conduit 90 is expanded in the valve 91 to about 12 bars and introduced into the fractionating column 92. In this column, equipped at the bottom with a steam coil 31 and at the head with a circulating water cooler 101, a liquid fraction rich in butanes is separated, withdrawn through the conduit 96 and, after cooling in the cooler 97, equipped with a water coil 98, passed through the conduit 99 to the expanding valve 100, then through the conduits 30 and 89 to the cold end of the exchanger 10.

The more volatile fraction, rich in propane, condensed in the cooler 101 is evacuated through the conduit 93. It is undercooled in the exchanger 86 by heat exchange with the residual nitrogen-methane mixture and flows then through the conduit 94 to the exchanger 57 where it is cooled again by the same mixture. It is then expanded in the valve 95 to the pressure of 7 bars and recombined with the liquid methane at the cold end of the exchanger 48.

The residual gas withdrawn from the head of the column 92 is combined through the conduit 102 and the expanding valve 103 to 7 bars to the liquid and gaseous low pressure fractions recycled at the cold end of the exchanger 10.

The gas mixture remaining in the separator 75 passes through the conduit 104 into the exchanger 10 where it is cooled and partly condensed, then through the conduit 105 to the separator 106. The liquid fraction rich in butanes and propane recovered from the separator passes through the conduit 107 to the exchanger 11 where it is undercooled, then expanded in the valve 108, and recombined through the conduit 109 with the gaseous mixture recycled at low pressure at the cold end of the exchanger 11.

The gas mixture remaining in the head of the separator 106 passes through the conduit 110 into the exchanger 11 and leaves the same through the conduit 111. A liquid fraction rich in propane and ethane is recovered in the separator 112. This fraction is passed through the conduit 113 into the exchanger 12 and after being undercooled in the same, is expanded in the valve 114 and added to the low pressure gas mixture at the cold end of the exchanger 12.

Finally, the residual gas withdrawn from the head of the separator 112 is introduced through the conduit 115 into the exchanger 12 where it is partly liquefied and then added through the conduit 116 to the liquefied natural gas expanded in the valve 23 and introduced together therewith through the conduit 24 into the separator 25.

Figure 2:
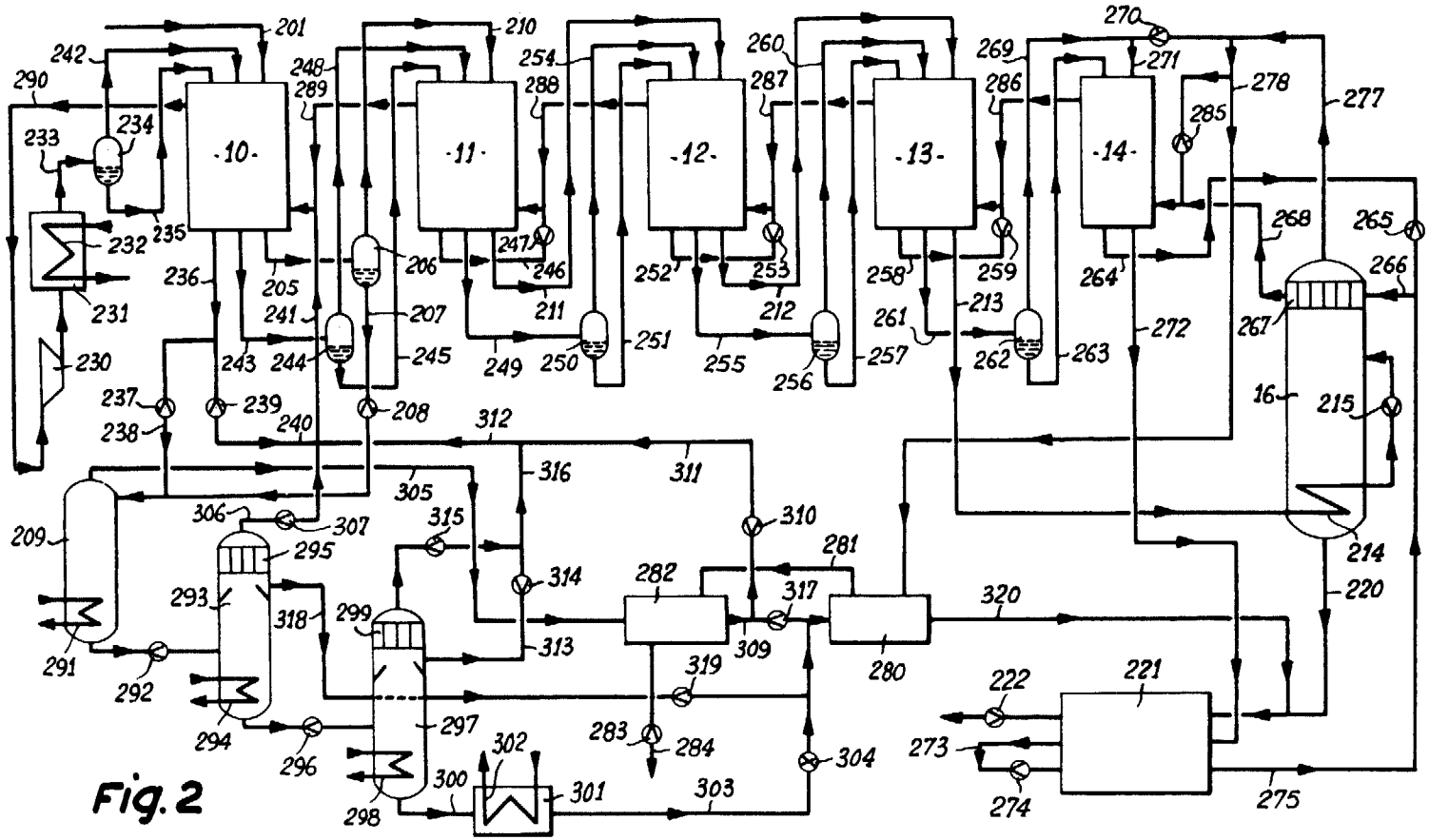
FIG. 2 shows an installation for liquefying natural gas in which the recycled gas passes through a closed circuit which is substantially independent of the natural gas circuit, and the connections between the natural gas circuit and the recycled gas circuit serve only to compensate the losses in the latter and to adjust its composition.

The installation of FIG. 2 comprises substantially the cooling and liquefying exchangers 10, 11, 12, 13 and 14, common to the natural gas and recycling gas circuits which are here completely separate, the tower 16 for extracting nitrogen from the liquefied natural gas and the fractionating columns 209, 293 and 297 for separating from the natural gas a fraction of heavy hydrocarbons before combining them with the liquid methane.

The natural gas to be liquefied, available at ambient temperature and at a pressure of about 50 bars, having a composition similar to that indicated above and containing also some $C_5$ and $C_6$ hydrocarbons, arrives through the conduit 201 in the exchanger 10 where it is cooled to $-12°$ C. and slightly condensed. It passes then through the conduit 205 into a separator 206. The condensate enriched in heavy hydrocarbons, passes through the conduit 207 and the expansion valve 208 to 15 bars to the head of a rectification column 209.

The column 209, heated at the bottom by a steam coil 291, separates the introduced liquid fraction into methane and ethane vapours and a liqud residual. The vapours withdrawn from the head through the conduit 305 are passed to an exchanger 282 where they are cooled by exchange with a residual methane and nitrogen mixture, whose origin will be explained further below. Withdrawn therefrom through conduit 309, they are then expanded to about 10 bars absolute in the valve 317 and after addition of heavier hydrocarbons (propane, butane, $C_5$ hydrocarbons) are liquefied and undercooled in the exchanger 280 in exchange with the same residual mixture, and finally are added through the conduit 320 to the liquid methane coming from the degasing tower 16.

One may divert a liquefied fraction of ethane and methane upstream of the expanding valve 317 and expand the same in a valve 310 to about 7 bars and add it through conduits 311, 312, and 241 to other hydrocarbons fractions which are recycled to the cold end of the exchanger 10.

The residual liquid separated in the sump of the column 209 is expanded in the valve 292 and introduced into a centre zone of the fractionating column 293, equipped with a water condenser and heated by a steam coil 294 which separates it into propane and lighter hydrocarbons on the one hand, and a fraction rich in butanes and heavier hydrocarbons on the other hand.

The propane condensed in the condenser 295 at the head of the column 293 is withdrawn through the conduit 318, then expanded in the valve 319 to 10 bars and added through the valve 304 to $C_5$ liquid hydrocarbons (and heavier) then added to the liquid methane and ethane mixture already mentioned at the warm end of the exchanger 280 for being undercooled and combined with the liquefied methane.

The uncondensable vapours coming from the head of the column 293 through the conduit 306 are expanded in the valve 307 to 7 bars and combined with the other recycled fractions at the cold end of the exchanger 10 through the conduit 241.

The liquid rich in butanes, taken from the bottom of the column 293, is expanded to 10 bars in the valve 296 and introduced into the fractionating column 297. This separates the butanes and lighter hydrocarbons from the $C_5$ and heavier hydrocarbons (benzoles). It has also a steam coil 298 for heating the sump and a water condenser 299.

The butanes condensed in the cooler 299 are withdrawn through the conduit 313 and expanded in the valve 314 to about 7 bars, then after adding through the expanding valve 315 the uncondensable gases coming from the head of the column 297, combined through the conduits 316, 312 and 241 with the other recycled fractions at the cold end of the exchanger 10 to compensate for inevitable butane and propane losses in the cycling gas.

The $C_5$ and heavier hydrocarbons withdrawn from the base of the column 297 pass through the conduit 300 to a cooler 301 with a circulating water coil 302 and after undercooling therein are combined through the conduit 303 and the valve 304 with the liquid propane fraction at the warm end of the exchanger 280.

The remaining natural gas evacuated from the separator 206 through the conduit 210 is further cooled in the exchanger 11 to about $-47°$ C., passes then through the conduit 211 into the exchanger 12 where it is cooled to about $-78°$ C., and liquefied. It then flows through the conduit 212 into the exchanger 13 where it is undercooled to $-105°$ C. It passes then through the conduit 213 to the coil 214 arranged in the sump of the degasing tower 16 where it is undercooled and heats the column.

It is finally expanded in the valve 215 to about 10 bars and introduced in to the centre part of this column.

In addition to the heating coil 216, the column 16 is equipped with a condenser 267 cooled by vaporizing a nitrogen-methane mixture boiling at −140° C. at 7 bars and coming from the closed cooling cycle. The liquefied natural gas is here separated into a liquid fraction practically free from nitrogen and nitrogen-rich vapours.

The liquid withdrawn from the base of the column 16 is passed through the conduit 220 to the sub-cooling exchanger 221. After addition of the previously separated and then undercooled heavier hydrocarbons through the conduit 320, the liquid is undercooled to about −161° C. in the exchanger 221 in exchange of heat with the methane-nitrogen cycle mixture and then expanded in the valve 222 at the inlet of the storage tank (not shown).

The methane and nitrogen vapours uncondenssed in the condenser 267 of the tower 16 are extracted through the conduit 227 and passed successively through the conduits 278 and 281 to the exchangers 280 and 282 where they are reheated to near ambient temperature, then expanded in the valve 283 and removed through the conduit 284 for use, for example, as fuel.

In view to reduce the nitrogen content of the cycling gas it is possible to add to these vapours through the expanding valve 270 a fraction of the gas coming from the separator 262 prior to its entry into the exchanger 14. Similarly, in order to increase the nitrogen content in the cycling gas, it is possible to remove a fraction of these methane and nitrogen vapours, to expand them in the valve 285 and to add them to the gas mixture coming from the condenser 267 of the degasing tower prior to vaporization and reheating in the exchanger 14.

The circuit of the gas mixture acting as refrigerating fluid is as follows:

The gas mixture is compressed by a turbo-compressor 230 to a pressure of about 30 bars absolute. It is then cooled in the cooler 231 with a circulating water coil 232 to about +30° C. and passed through the conduit 233 to the separator 244.

The liquid recovered in the separator is introduced through the conduit 235 into the exchanger 10 where it is undercooled to about −12° C. After evacuation through the conduit 236, it is combined through the expanding valve 239 at 6 bars and the conduits 240 and 241 with the low-pressure recycled gas arriving through the conduit 289 at the cold end of the exchanger 10 for being vaporized so as to contribute to the cooling effect of this exchanger. However, a fraction may be passed through the expanding valve 237 and the conduit 238 to the fractioning column 209 for regulating the composition of the gas mixture of the refrigerating cycle, if the same contains too much high boiling products.

The gas mixture of the cycle leaves the separator 234 through the conduit 242, is then cooled in the exchanger 10 to about −12° C. and undergoes partial condensation. It passes then through the conduit 243 to the separator 244. The liquid fraction recovered in the separator passes through the conduit 245 to the exchanger 11 where it is undercooled to −47° C. and is then combined through the conduit 246 and the expanding valve 247 with the low pressure recycling gas at the cold end of the exchanger 11.

The cycling gas remaining passes through the conduit 248 to the exchanger 11 where it is cooled to −47° C. and again partly condensed, and then through the conduit 249 to the separator 250. The recovered liquid fraction flows from this separator through the conduit 251 to the exchanger 12 where it is undercooled to about −78° C., is then combined through the conduit 252 and the expanding valve 253 to the cold low-pressure cycling gas at the cold end of the exchanger 12.

The cycling gas removed from the head of the separator 250 through the conduit 254 is cooled again to −78° C. and partly condensed in the exchanger 12. It is introduced through the conduit 255 into the separator 256. The liquid fraction recovered in this separator passes through the conduit 257 to the exchanger 13 where it is undercooled to about −105° C. and then combined through the conduit 258 and the expanding valve 259 with the low-pressure cold recycling gas at the cold end of the exchanger 13.

The remaining cycling gas evacuated from the head of the separator 256 through the conduit 260 is cooled to −105° C. and mainly condensed in the exchanger 13, and then passed through the conduit 261 to the separator 262. The liquid recovered in this separator is introduced through the conduit 263 into the exchanger 14 where it is undercooled to about −132° C. and then through the conduit 264, the expanding valve 265 and the conduit 266 to the condenser 267 at the head of the degasing tower 16, after addition through the conduit 275 of another methane-nitrogen fraction, the origin of which will be explained below.

The residual gas from the separator 262 is evacuated through the conduit 269 towards the exchanger 14 where it is cooled to about −132° C. and condensed. The liquid flows through the conduit 272 to the exchanger 221. It is first undercooled concurrently with the liquefied natural gas, then raised in countercurrent through the conduit 273 and the expansion valve 274 to 7 bars through the same exchanger, ensuring the undercooling of both these liquids to about −160° C. After partial vaporization it is added through the conduit 275 to the liquid introduced through the conduit 266 into the condenser 267 of the degasing tower 16.

The nitrogen-methane mixture already partly vaporized in the condenser 267 and evacuated through the conduit 268 flows to the cold end of the exchanger 14 and is totally vaporized and reheated. The gaseous low-pressure recycling mixture is then introduced successively into the exchangers 13, 12, 11, and 10 through the conduits 286, 287, 288 and 289, after addition of condensed and undercooled liquid fractions coming from the separators 256, 250, 244 and 234 as indicated above. After warming up to ambient temperature the gaseous cycling mixture passes through the conduit 290 to the turbo-compressor 230.

What we claim is:

[1. In a method for cooling a gaseous mixture to low temperature and producing at least one constituent of this mixture in liquid phase, comprising subjecting a first gaseous mixture to a fractionate condensation in a plurality of heat-exchange stages with at least one of the condensed fractions being expanded to a first pressure and vaporized in heat exchange with said first gaseous mixture undergoing fractionate condensation, expanding to a second pressure said at least one constituent after its condensation and withdrawing said expanded constituent as product, said first pressure being substantially higher than said second pressure, thereafter recompressing said at least one fraction to a third pressure substantially higher than said first pressure, and recombining said recompressed fraction with said first gaseous mixture; the improvement comprising progressively cooling a second gaseous mixture in a plurality of heat-exchange stages with said first mixture, said second mixture having the same main components as said first mixture, and maintaining said first gaseous mixture with said second gaseous mixture separate at least until they are under conditions of temperature and pressure such that said constituent to be produced in liquid phase is at least mostly condensed within said second gaseous mixture and said at least one condensed fraction has been withdrawn from said first gaseous mixture for expansion and vaporization.]

[2. A method as claimed in claim 1, said second gaseous mixture being initially at a fourth pressure substantially higher than said third pressure.]

[3. A method as claimed in claim 1, in which said first gaseous mixture flows within a closed cycle and all the expanded and vaporized fractions separated from said first gaseous mixture are reunited to reconstitute said first gaseous mixture.]

[4. A method as claimed in claim 3, in which said second gaseous mixture is subjected to a fractionate condensation, and adding at least a part of a fraction separated from said second gaseous mixture during fractionate condensation to an expanded fraction of said first gaseous mixture undergoing vaporization, thereby to compensate for losses in said closed cycle and to adjust its composition.]

[5. A method as claimed in claim 3, and adding at least a fraction separated during the fractionate condensation of said first gaseous mixture to a fraction separated from said second gaseous mixture at such a flow rate as to adjust the composition of said first gaseous mixture.]

[6. A method of utilizing a first gaseous mixture at relatively low pressure to refrigerate a second gaseous mixture at relatively high pressure, comprising establishing a refrigeration cycle in which said first gaseous mixture is subjected to fractionate condensation in a plurality of heat exchange stages with at least one of the condensed fractions being expanded and vaporized in heat exchange with said first gaseous mixture undergoing fractionate condensation, then recompressed to said relatively low pressure and reunited with said first gaseous mixture, and progressively cooling said second mixture in a plurality of said heat exchange stages.]

[7. A method as claimed in claim 6, and combining said first and second gaseous mixtures downstream of a plurality of said heat exchange stages.]

*8. A method for cooling a second gaseous mixture to low temperature and producing at least one constituent of said mixture in liquid phase, comprising:*

*a. cooling and subjecting a first gaseous mixture containing at least one component of said second gaseous mixture, to a fractionate condensation under a first pressure,*

*b. expanding at least two condensed fractions obtained during the fractionate condensation of said first gaseous mixture, reuniting the expanded condensed fractions with said first gaseous mixture under a second pressure lower than said first pressure, vaporizing and reheating the reunited fractions with said first gaseous mixture under said second pressure, by heat exchange with said second gaseous mixture undergoing cooling, and with said first gaseous mixture undergoing fractionate condensation, and recompressing said first gaseous mixture to said first pressure,*

*c. reuniting under said first pressure said second gaseous mixture undergoing cooling with said first gaseous mixture undergoing fractionate condensation, when said gaseous mixture is in conditions of temperature and pressure such that a major portion of said constituent to be produced in liquid phase is condensed within said second gaseous mixture, and after the first condensed fraction of said first gaseous mixture has been withdrawn for expansion and vaporization, continuing the fractionate condensation of the mixture so obtained under said first pressure until there is obtained a last condensed fraction containing a major part of said constituent to be produced in liquid phase,*

*d. expanding to said second pressure the last condensed fraction, and separating the last expanded fraction into a liquid portion expanded to a pressure lower than said second pressure and a residual gaseous portion for recompression with said first gaseous mixture, and withdrawing said last expanded liquid portion as a product stream, and*

*e. prior to reuniting said first gaseous mixture and said second gaseous mixture, condensing at least partially said second gaseous mixture under a third pressure which is higher than said first pressure, and expanding said second gaseous mixture at least partially condensed to said first pressure.*

*9. In a method for cooling a second gaseous mixture to low temperature and producing at least one constituent of said mixture in liquid phase, comprising:*

*a. cooling said second gaseous mixture until at least a major portion of said consituent to be produced in liquid phase is condensed within said second gaseous mixture, then expanding at least said condensed constituent to a first pressure,*

*b. cooling and subjecting a first gaseous mixture comprising at least one component of said second gaseous mixture, to a fractionate condensation under a second pressure which is higher than said first pressure,*

*c. expanding at least two condensed fractions obtained during the fractionate condensation of said first gaseous mixture, reuniting the expanded fractions with said first gaseous mixture under a third pressure which is intermediate said first and second pressures, vaporizing and reheating the reunited fractions with said first gaseous mixture under said third pressure by heat exchange with said second gaseous mixture undergoing cooling and with said first gaseous mixture undergoing fractionate condensation and recompressing said first gaseous mixture to said second pressure, the improvement comprising adjusting the composition of said first gaseous mixture in at least one component:*

*d. when there is an insufficient quantity of said component, subjecting said second gaseous mixture undergoing cooling to fractionate condensation, rectifying at least a part of a condensed fraction of said second gaseous mixture under at least a pressure intermediate said second and third pressure, adding at least a part of a fraction separated during said rectification to said first gaseous mixture, and*

*e. when there is an excess of said constituent, rectifying at least a part of a condensed fraction of said first gaseous mixture under at least a pressure intermediate said second and third pressures, and adding at least a part of a fraction separated during said rectification to said second gaseous mixture.*

* * * * *